(12) United States Patent
Lecomte et al.

(10) Patent No.: US 10,758,377 B2
(45) Date of Patent: *Sep. 1, 2020

(54) FRICTIONLESS VERTICAL SUSPENSION MECHANISM FOR PROSTHETIC FEET

(71) Applicant: Össur Iceland ehf, Reykjavik (IS)

(72) Inventors: Christophe Lecomte, Reykjavik (IS); Benedikt Skulason, Reykjavik (IS); Jeroen Nijman, Reykjavik (IS)

(73) Assignee: Össur Iceland ehf, Reykjavik (IS)

( * ) Notice: Subject to any disclaimer, the term of this patent is extended or adjusted under 35 U.S.C. 154(b) by 72 days.

This patent is subject to a terminal disclaimer.

(21) Appl. No.: 15/981,723

(22) Filed: May 16, 2018

(65) Prior Publication Data

US 2018/0360624 A1 Dec. 20, 2018

Related U.S. Application Data

(63) Continuation of application No. 14/699,319, filed on Apr. 29, 2015, now Pat. No. 9,999,523, which is a
(Continued)

(51) Int. Cl.
*A61F 2/66* (2006.01)
*A61F 2/60* (2006.01)
*A61F 2/50* (2006.01)

(52) U.S. Cl.
CPC ........ *A61F 2/66* (2013.01); *A61F 2002/5003* (2013.01); *A61F 2002/5079* (2013.01);
(Continued)

(58) Field of Classification Search
CPC ................ A61F 2/66; A61F 2002/5079; A61F 2002/6664; A61F 2002/6657; A61F 2/60
See application file for complete search history.

(56) References Cited

U.S. PATENT DOCUMENTS

| 35,686 | A | 6/1862 | Jewettt |
| 53,931 | A | 4/1866 | Weston |

(Continued)

FOREIGN PATENT DOCUMENTS

| DE | 817186 | 10/1951 |
| DE | 834884 | 3/1952 |

(Continued)

OTHER PUBLICATIONS

Dec. 17, 2012 International Search Report and Written Opinion for International Application No. PCT/US12/57149 filed on Sep. 25, 2012.

(Continued)

*Primary Examiner* — Bruce E Snow
(74) *Attorney, Agent, or Firm* — Knobbe, Martens, Olson & Bear, LLP (57) ABSTRACT

A vertical suspension system for a prosthetic foot includes a first member operatively coupleable to an amputee's residual leg. The suspension system can also include a second member coupleable to a prosthetic foot. One or more upper leaf springs and one or more lower leaf springs extend between and are attached to the first and second members such that at least one of the ends of each leaf spring is rotationally fixed to the first or second members, where the upper an lower leaf springs are spaced apart from each other.

18 Claims, 11 Drawing Sheets

Related U.S. Application Data continuation of application No. 13/626,567, filed on Sep. 25, 2012, now Pat. No. 9,028,559.

(60) Provisional application No. 61/539,207, filed on Sep. 26, 2011.

(52) U.S. Cl.
CPC .............. *A61F 2002/6614* (2013.01); *A61F 2002/6657* (2013.01); *A61F 2002/6664* (2013.01)

(56) References Cited

U.S. PATENT DOCUMENTS

| | | | |
|---|---|---|---|
| 57,666 A | 9/1866 | Bly | |
| 368,580 A | 8/1887 | Frees | |
| 411,377 A | 9/1889 | Fairchild | |
| 809,876 A | 1/1906 | Wilkins | |
| 987,893 A | 3/1911 | Lawrence | |
| 1,023,247 A | 4/1912 | Frees | |
| 1,779,765 A | 10/1930 | Eichhorn | |
| 2,490,796 A | 12/1949 | Gettman et al. | |
| 2,529,968 A | 11/1950 | Sartin | |
| 2,573,347 A | 10/1951 | Mazzola | |
| 2,605,474 A | 8/1952 | Oliver | |
| 2,619,652 A | 12/1952 | Vesper | |
| 2,620,485 A | 12/1952 | Greissinger et al. | |
| 2,692,392 A | 10/1954 | Bennington et al. | |
| 2,851,694 A | 6/1955 | Valenti | |
| 2,731,645 A | 1/1956 | Woodall | |
| 3,480,972 A | 12/1969 | Prahl et al. | |
| 3,551,914 A | 1/1971 | Woodall | |
| 3,784,988 A | 1/1974 | Trumpler | |
| 3,874,004 A | 4/1975 | May | |
| 3,990,116 A | 11/1976 | Fixel et al. | |
| 4,026,534 A * | 5/1977 | Barnwell ............... | B60R 19/26 267/139 |
| 4,145,765 A | 3/1979 | Malone | |
| 4,652,266 A | 3/1987 | Truesdell | |
| 5,037,444 A | 8/1991 | Phillips | |
| 5,139,525 A | 8/1992 | Kristinsoon | |
| 5,156,630 A | 10/1992 | Rappoport et al. | |
| 5,156,632 A | 10/1992 | Wellershaus | |
| 5,181,933 A | 1/1993 | Phillips | |
| 5,219,365 A | 6/1993 | Sabolich | |
| 5,376,133 A | 12/1994 | Gramnas | |
| 5,376,141 A | 12/1994 | Phillips | |
| 5,509,936 A | 4/1996 | Rappoport et al. | |
| 5,549,711 A * | 8/1996 | Bryant .................... | A61F 2/66 623/53 |
| 5,653,768 A | 8/1997 | Kania | |
| 5,746,774 A | 5/1998 | Kramer et al. | |
| 5,800,568 A | 9/1998 | Atkinson et al. | |
| 5,800,570 A | 9/1998 | Collier | |
| 5,897,594 A | 4/1999 | Martin et al. | |
| 5,948,021 A | 9/1999 | Radcliffe | |
| 6,077,301 A | 6/2000 | Pusch | |
| 6,187,052 B1 | 2/2001 | Molino et al. | |
| 6,241,776 B1 | 6/2001 | Christensen | |
| 6,306,178 B1 | 10/2001 | Kania et al. | |
| 6,350,286 B1 | 2/2002 | Atkinson et al. | |
| 6,402,790 B1 | 6/2002 | Celebi | |
| 6,436,149 B1 | 8/2002 | Rincoe | |
| 6,443,993 B1 | 9/2002 | Koniuk | |
| 6,482,236 B2 | 11/2002 | Habecker | |
| 6,527,811 B1 | 3/2003 | Phillips | |
| 6,562,075 B2 | 5/2003 | Townsend et al. | |
| 6,596,029 B1 | 7/2003 | Gramnas | |
| 6,602,295 B1 | 8/2003 | Doddroe et al. | |
| 6,719,807 B2 | 4/2004 | Harris | |
| 6,764,521 B2 | 7/2004 | Molino et al. | |
| 6,764,522 B1 | 7/2004 | Cehn | |
| 6,767,370 B1 | 7/2004 | Mosler et al. | |
| 6,805,717 B2 | 10/2004 | Christensen | |
| 6,855,170 B2 | 2/2005 | Gramnas | |
| 6,863,695 B2 | 3/2005 | Arbogast et al. | |
| 6,929,665 B2 | 8/2005 | Christensen | |
| 6,942,704 B2 | 9/2005 | Sulprizio | |
| 6,966,933 B2 | 11/2005 | Christensen | |
| 7,172,630 B2 | 2/2007 | Christensen | |
| 7,341,603 B2 | 3/2008 | Christensen | |
| 7,347,877 B2 | 3/2008 | Clausen et al. | |
| 7,364,593 B2 | 4/2008 | Claudino et al. | |
| 7,410,503 B2 | 8/2008 | Townsend et al. | |
| 7,419,509 B2 | 9/2008 | Christensen | |
| 7,431,737 B2 | 10/2008 | Ragnarsdottir et al. | |
| 7,507,259 B2 | 3/2009 | Townsend et al. | |
| 7,520,904 B2 | 4/2009 | Christensen | |
| 7,578,852 B2 | 8/2009 | Claudino et al. | |
| 7,611,543 B2 | 11/2009 | Claudino et al. | |
| 7,637,959 B2 | 12/2009 | Clausen et al. | |
| 7,686,848 B2 | 3/2010 | Christensen | |
| 7,708,784 B2 | 5/2010 | Claudino et al. | |
| 7,763,082 B1 | 7/2010 | Curtis | |
| 7,819,926 B1 | 10/2010 | Longino | |
| 7,824,446 B2 | 11/2010 | Boren et al. | |
| 7,846,213 B2 | 12/2010 | Lecomte et al. | |
| 7,862,621 B2 | 1/2011 | Grab et al. | |
| 7,954,502 B2 | 6/2011 | Claudino et al. | |
| 7,955,399 B2 | 6/2011 | Claudino et al. | |
| 7,963,998 B2 | 6/2011 | Boiten | |
| 7,985,264 B2 | 7/2011 | Cheng et al. | |
| 8,574,314 B2 | 11/2013 | Townsend et al. | |
| 9,028,559 B2 * | 5/2015 | Lecomte ................ | A61F 2/66 623/38 |
| 9,375,989 B2 | 6/2016 | Skulason | |
| 9,999,523 B2 * | 6/2018 | Lecomte ................ | A61F 2/66 |
| 2002/0087216 A1 | 7/2002 | Adelson et al. | |
| 2002/0143406 A1 | 10/2002 | Townsend et al. | |
| 2003/0144745 A1 | 7/2003 | Phillips | |
| 2004/0044417 A1 | 3/2004 | Gramnas | |
| 2004/0054423 A1 | 3/2004 | Martin | |
| 2004/0064195 A1 | 4/2004 | Herr | |
| 2004/0068326 A1 | 4/2004 | Christensen | |
| 2004/0225375 A1 | 11/2004 | Chen | |
| 2004/0225376 A1 | 11/2004 | Townsend et al. | |
| 2004/0236435 A1 | 11/2004 | Chen | |
| 2004/0243253 A1 | 12/2004 | Cool et al. | |
| 2005/0038525 A1 | 2/2005 | Doddroe et al. | |
| 2005/0203640 A1 | 9/2005 | Christensen | |
| 2006/0015192 A1 | 1/2006 | Clausen et al. | |
| 2006/0030950 A1 | 2/2006 | Townsend et al. | |
| 2006/0041321 A1 | 2/2006 | Christensen | |
| 2006/0069448 A1 | 3/2006 | Yasui | |
| 2006/0173555 A1 | 8/2006 | Harn et al. | |
| 2006/0185703 A1 | 8/2006 | Claudino et al. | |
| 2006/0212131 A1 | 9/2006 | Curtis | |
| 2006/0224246 A1 | 10/2006 | Clausen et al. | |
| 2006/0235544 A1 | 10/2006 | Iversen et al. | |
| 2006/0249315 A1 | 11/2006 | Herr et al. | |
| 2007/0043449 A1 | 2/2007 | Herr et al. | |
| 2007/0100466 A1 | 5/2007 | Allert | |
| 2007/0213840 A1 | 9/2007 | Townsend et al. | |
| 2008/0004718 A1 | 1/2008 | Mosler | |
| 2008/0140222 A1 | 6/2008 | Gramnas | |
| 2008/0228287 A1 | 9/2008 | Ninomiya | |
| 2008/0262635 A1 | 10/2008 | Moser et al. | |
| 2008/0281436 A1 | 11/2008 | Claudino et al. | |
| 2008/0306612 A1 | 12/2008 | Mosler | |
| 2009/0012630 A1 | 1/2009 | Mosler et al. | |
| 2009/0105845 A1 | 4/2009 | Curtis | |
| 2009/0204229 A1 | 8/2009 | Mosler et al. | |
| 2009/0204231 A1 | 8/2009 | Bonacini | |
| 2009/0265019 A1 | 10/2009 | Chritstensen | |
| 2009/0287315 A1 | 11/2009 | Lecomte et al. | |
| 2010/0023135 A1 | 1/2010 | Rubie et al. | |
| 2010/0030343 A1 | 2/2010 | Childress et al. | |
| 2010/0042228 A1 | 2/2010 | Colvin et al. | |
| 2010/0174385 A1 | 7/2010 | Casler et al. | |
| 2010/0179668 A1 | 7/2010 | Barhart et al. | |
| 2011/0071650 A1 | 3/2011 | Claudino et al. | |
| 2011/0107581 A1 | 5/2011 | Williams et al. | |
| 2011/0166674 A1 | 7/2011 | Montmartin | |

(56) References Cited

U.S. PATENT DOCUMENTS

| | | |
|---|---|---|
| 2011/0295385 A1 | 12/2011 | Herr et al. |
| 2012/0016493 A1 | 1/2012 | Hansen et al. |
| 2012/0078380 A1 | 3/2012 | Jonsson et al. |
| 2013/0085581 A1 | 4/2013 | Lecomte |

FOREIGN PATENT DOCUMENTS

| | | |
|---|---|---|
| DE | 920651 | 11/1954 |
| DE | 298 20 904 | 6/1999 |
| GB | 117547 | 8/1918 |
| GB | 120462 | 11/1918 |
| WO | WO 91/15171 | 10/1991 |
| WO | WO 1995/08967 | 4/1995 |
| WO | WO 2011/066354 | 6/2011 |

OTHER PUBLICATIONS

Nov. 8, 2013 International Search Report and Written Opinion for PCT Application No. PCT/US2013/052750 filed Jul. 30, 2013.

Jul. 13, 2015 Partial Supplementary European Search Report for Application No. 12835295.2 Filed Apr. 16, 2014.

\* cited by examiner

FIG. 7B

FRICTIONLESS VERTICAL SUSPENSION MECHANISM FOR PROSTHETIC FEET

CROSS-REFERENCE TO RELATED APPLICATIONS

This application is a continuation application of U.S. patent application Ser. No. 14/699,319, now U.S. Pat. No. 9,999,523, filed on Apr. 29, 215, entitled "FRICTIONLESS VERTICAL SUSPENSION MECHANISM FOR PROSTHETIC FEET" which is a continuation of U.S. patent application Ser. No. 13/626,567, filed on Sep. 25, 2012, entitled "FRICTIONLESS VERTICAL SUSPENSION MECHANISM FOR PROSTHETIC FEET", now U.S. Pat. No. 9,028,559, which claims priority benefit of U.S. Provisional Application No. 61/539,207, filed Sep. 26, 2011, entitled "FRICTIONLESS VERTICAL SUSPENSION MECHANISM FOR PROSTHETIC FEET", the entirety of each of which is hereby incorporated by reference herein.

BACKGROUND

Field

The present application relates in certain embodiments to prosthetic devices. In particular, the present application in certain embodiments relates to a frictionless vertical suspension mechanism for a prosthetic foot.

Description of the Related Art

Prosthetic feet of different designs are well known in the art. The various conventional designs have sought to solve various limitations associated with prosthetic feet.

Some prosthetic foot designs employ shock absorbing members (e.g., ankle members). However, such shock absorbing members tend to be relatively heavy and/or bulky. A common problem observed in prosthetic feet aiming for high travel suspension is that when in mid-stance, the bodyweight is supported by both the toe and the heel, but at heel strike or toe-off the weight is only supported by the respective part of the prosthetic foot. Therefore, the foot will be significantly stiffer at mid-stance than at heel strike or toe-off. This can cause an "obstacle" like feeling in the mid-stance of the rollover of the foot. Existing prosthetic feet with vertical suspension shock absorbers are also heavy with relatively high energy losses from, for example, the foot hitting the ground and friction within the suspension system, and are therefore arguably not well suited for high active use, such as running.

Accordingly, there is a need for an improved shock absorbing member for a prosthetic foot that is lightweight and provides frictionless vertical suspension regardless of the direction of the force on the prosthetic foot, and a need for a prosthetic foot incorporating the improved shock absorbing member that has rollover characteristics fit for everyday use and that encourages highly active use (e.g., running) through its suspension, energy return and light weight.

SUMMARY

In accordance with one embodiment, a lightweight, low energy loss, vertical suspension system for prosthetic feet is provided. The vertical suspension system enables rollover characteristics between heel strike and toe-off of a prosthetic foot that are fit for everyday use and at the same time encourage highly active users (e.g., in running) through its suspension, energy return and light weight. The substantially frictionless nature of the vertical suspension system results in substantially greater energy return than prior art alternative suspension systems. As a result, the vertical suspension system is well-suited for physically demanding activities such as running.

In accordance with another embodiment, a vertical suspension system for a prosthetic foot is provided. The suspension system comprises a first member having an upper coupling location and a lower coupling location wherein the first member is adapted to be operatively coupled to an amputee's residual leg. The suspension system also comprises a second member having an upper coupling location and a lower coupling location wherein the second member is adapted to be coupled to the prosthetic foot. At least one upper leaf spring having a first end portion and a second end portion located on opposite ends of the upper leaf spring is coupled to the first member's upper coupling location and to the second member's upper coupling location. At least one of the upper leaf spring's first end portion and second end portion is rotationally fixed to at least one of the first member and the second member. At least one lower leaf spring having a first end portion and a second end portion located on opposite ends of the lower leaf spring is coupled to the first member's lower coupling location and to the second member's lower coupling location. At least one of the lower leaf spring's first end portion and second end portion is rotationally fixed to at least one of the first member and the second member.

In accordance with another embodiment, a prosthetic foot is provided. The prosthetic foot comprises a foot plate extending from a generally vertical proximal portion to a generally horizontal distal portion, the foot plate curving downwardly and forwardly between the proximal and distal portions. The prosthetic foot also comprises an adapter operably coupleable to the proximal portion of the prosthetic foot and disposed forwardly of said proximal portion, the adapter operably coupleable to a prosthetic socket. The prosthetic foot further comprises a plurality of parallel leaf springs that operably interconnect the adapter and the proximal portion of the prosthetic foot, the leaf springs spaced apart from each other and extending generally horizontally between the adapter and the proximal portion of the prosthetic foot.

In accordance with still another embodiment, a vertical suspension system is provided. The suspension system comprises a first member having an upper coupling location and a lower coupling location, and a second member having an upper coupling location and a lower coupling location wherein the second member is configured to be fixedly coupled to a support component, the first member being movable relative to the second member. The suspension system also comprises at least one upper leaf spring having a first end portion and a second end portion located on opposite ends of the upper leaf spring, wherein the upper leaf spring is coupled to the first member's upper coupling location and to the second member's upper coupling location. At least one of the upper leaf spring's first end portion and second end portion is rotationally fixed to at least one of the first member and the second member. The suspension system also comprises at least one lower leaf spring having a first end portion and a second end portion that are located on opposite ends of the lower leaf spring, wherein the lower leaf spring is coupled to the first member's lower coupling location and to the second member's lower coupling location. At least one of the lower leaf spring's first end portion and second end portion is rotationally fixed to at least one of the first member and the second member.

DETAILED DESCRIPTION OF SOME EXEMPLIFYING EMBODIMENTS

An objective of one or more embodiments described below is to provide a lightweight, low energy loss, vertical suspension system for prosthetic feet. The vertical suspension system enables rollover characteristics between heel strike and toe-off that are fit for everyday use and at the same time encourage highly active users through its suspension, energy return and lightness. Additionally, the substantially frictionless nature of the vertical suspension system results in substantially greater energy return than existing suspension systems, and is therefore well-suited for physically demanding activities such as running.

Figure 1A:
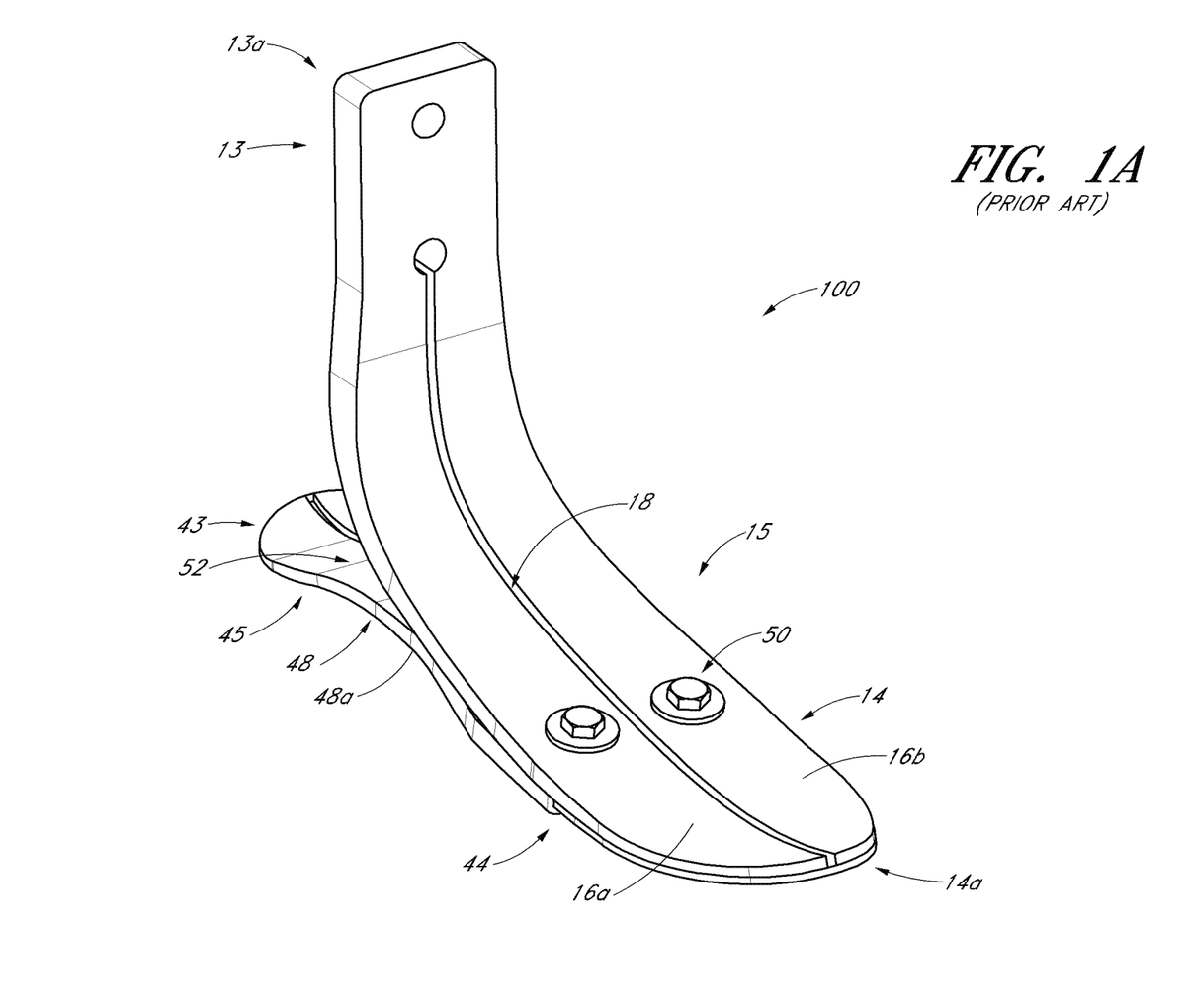
FIG. 1A is a schematic perspective front view of a conventional prosthetic foot.

FIG. 1A shows a conventional prosthetic foot 100. The prosthetic foot 100 can have a foot member 15 that extends from a proximal section 13 to a distal section 14. In the illustrated embodiment, the proximal section 13 can be generally vertically oriented, and the distal section 14 can be generally horizontally oriented with the foot member 15 curving downward from the proximal section 13 to the distal section 14. The proximal section 13 can extend to a proximal end 13a and be generally at a location of a natural human ankle. In one embodiment, the distal section 14 can extend to a distal end 14a generally at a location of natural human toes.

With continued reference to FIG. 1A, the foot member 15 can have multiple elongate segments that can flex independently relative to each other. In the illustrated embodiment, the foot member 15 has two elongate segments 16a, 16b that are separated from each other by a slot 18 that extends along a length between the distal end 14a and the proximal end 13a of the foot member 15. In one embodiment, the slot 18 extends along the entire length of the foot member 15. In another embodiment, the slot 18 extends along a length that is shorter than the entire length of the foot member 15. In one embodiment, the slot 18 extends linearly along its length, so that the width of all the elongate segments 16a, 16b is generally the same.

The prosthetic foot 100 can also have a heel member 45 that extends between a proximal end 43 and a distal end 44 and is disposed below at least a portion of the foot member 15. In one embodiment, the heel member 45 can be coupled to the foot member 15 via one or more fasteners 50 (e.g., bolts) at a location between the proximal and distal ends 13a, 14a of the foot member 15 such that the heel member is cantilevered relative to the foot member 15 and extends to a free rear end at the proximal end 43. The heel member 45 can have a curvilinear profile along its length that defines an arch 48 between the proximal and distal ends 43, 44. The foot and heel members 15, 45 can define a slot 52 therebetween in the fore-aft direction at a rear portion of the prosthetic foot 100. In one embodiment, the slot 52 can taper toward a front end of the prosthetic foot 100. A resilient member (not shown) can be interposed between the heel member 45 and the foot member 15 within the slot 52. In one embodiment, the resilient member can separate at least a portion of the foot member 15 from the heel member 45. In another embodiment, the resilient member can completely separate the foot member 15 from the heel member 45.

In one embodiment, the foot and heel members 15, 45 are plate-like members with generally planar top and bottom surfaces and generally rectangular transverse cross-sections. The foot and heel members 15, 45 can be made of lightweight resilient materials, such as graphite, fiberglass, carbon fiber and the like. In some embodiments, the foot and heel members 15, 45 can be formed of multiple layers of material that define a monolithic piece.

Figure 1B:
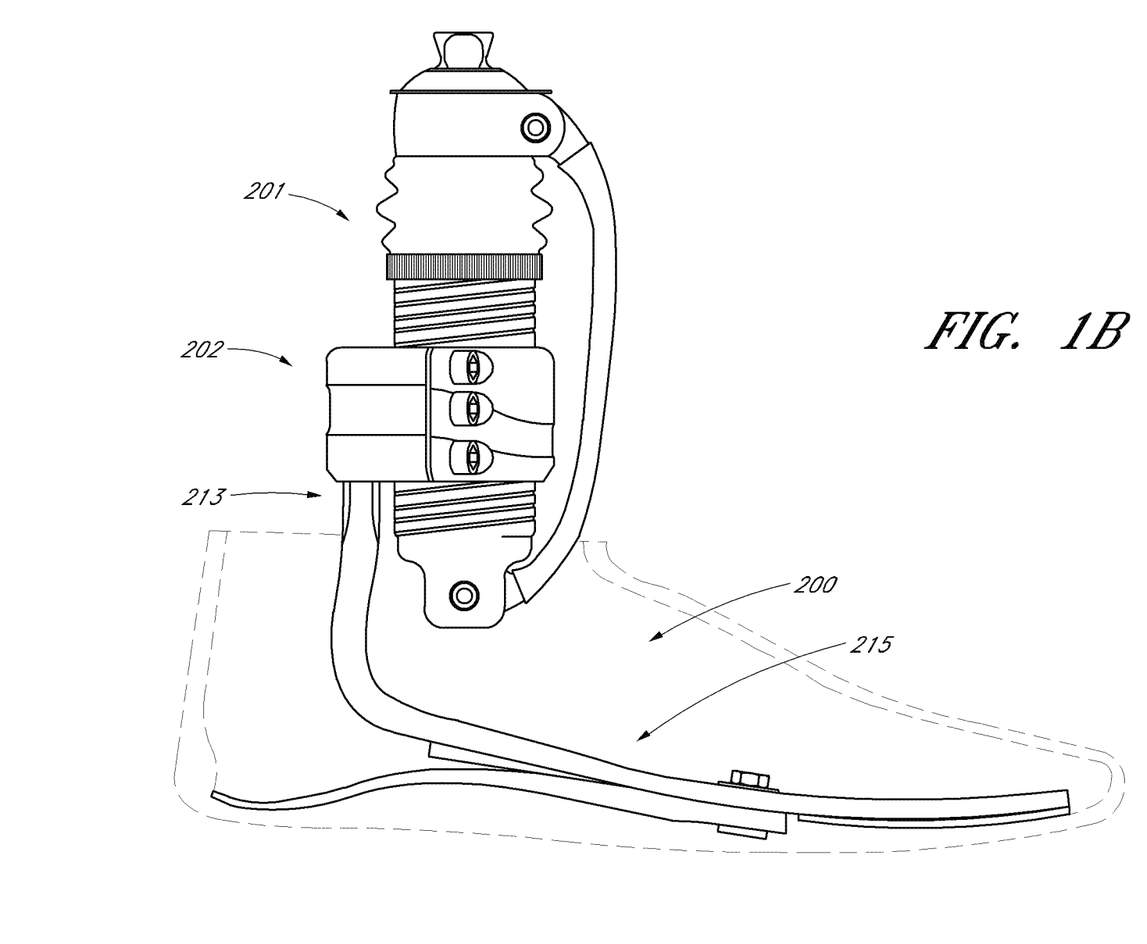
FIG. 1B is a schematic side view of a prosthetic foot including a shock module.

FIG. 1B shows an example of a prosthetic foot 200 including a shock member 201 operatively coupled to the proximal section 213 of the foot member 215. In the illustrated embodiment, the shock module 201 extends generally vertically and includes an attachment clamp 202. The shock module 201 can couple to the foot member 215 via one or more fasteners (e.g., threaded fasteners), as further described below. In another embodiment, the vertical suspension module 201 can couple to the foot member 215 with an adhesive (e.g., glue, epoxy). In still another embodiment, for example as shown in FIG. 1B, the attachment clamp 202 of the vertical suspension module 201 can have a recess that receives at least a portion of the proximal section 213 of the foot member 215 therein. The shock module 201 can include an inner pylon and outer pylon. The shock module 201 can further include a resilient element, for example, a compressible coil spring and/or a compressible fluid coupled to or fixed with respect to the inner pylon. In use, the resilient element can provide for vertical shock absorption and energy return.

In one embodiment, the prosthetic foot 100, 200 can be coupled (e.g., removably coupled) to a cosmesis foot cover (not shown) that has an upper portion and a sole portion. In one embodiment, the sole portion can have an insole with a convex surface that corresponds to the curvature of a concave bottom surface 48a of the arch 48 of the heel member 45, such that the insole maintains contact with the bottom surface 48a of the heel member 45 during ambulation of the prosthetic foot 100, 200 from heel strike to toe-off.

Further details on prosthetic feet can be found in U.S. Publication 2005/0038524, U.S. Pat. No. 7,846,213, U.S.

application Ser. No. 13/034,474, filed Feb. 24, 2011 and titled "Prosthetic Foot with a Curved Split," and U.S. application Ser. No. 13/149,118, filed May 31, 2011 and titled "Height-adjustable Threaded Shock Absorbing Module and Associated Coupling Member," the entire contents of all of which are hereby incorporated by reference and should be considered a part of this specification. Further details of foot covers and insole portions can be found in US Publication 2010/0004757 titled "Smooth Rollover Insole for Prosthetic Foot" and US Publication 2006/0015192 titled "Functional Foot Cover," the entire contents of all of which are hereby incorporated by reference and should be considered a part of this specification.

FIGS. 2-5 illustrate example embodiments of a vertical suspension member 1 attached to the prosthetic foot member 15. The vertical suspension member 1 can provide certain benefits over other suspension systems, such as the shock module 201 shown in FIG. 1B. For example, the vertical suspension member 1 can be lighter in weight than other suspension systems and can be more dynamic as a result of less friction created in the vertical suspension member 1 compared to other suspension systems. The vertical suspension member 1 can include a first member 11 and a second member 12. The first member 11 can be attached to a person's body, for example, attached to a person's leg below the person's knee. For example, a socket-style stump attachment system can be provided that attaches to a stump of the person's residual limb. The stump attachment system can include a socket at one end and a metal rod (e.g., approximately 25.5 mm in diameter) at the other end. The metal rod can be removably received into a cylindrical cavity 17 (see FIG. 3) in the first member 11. For example, the metal rod may screw into the cylindrical cavity 17 or screws may secure the metal rod inside the cylindrical cavity 17. In another embodiment, a male pyramid connector (not shown) can be inserted into the cavity 17 and threadably coupled to the first member 11, and a user's stump can be coupled to the pyramid connector (e.g., via a pylon member).

Figure 2:
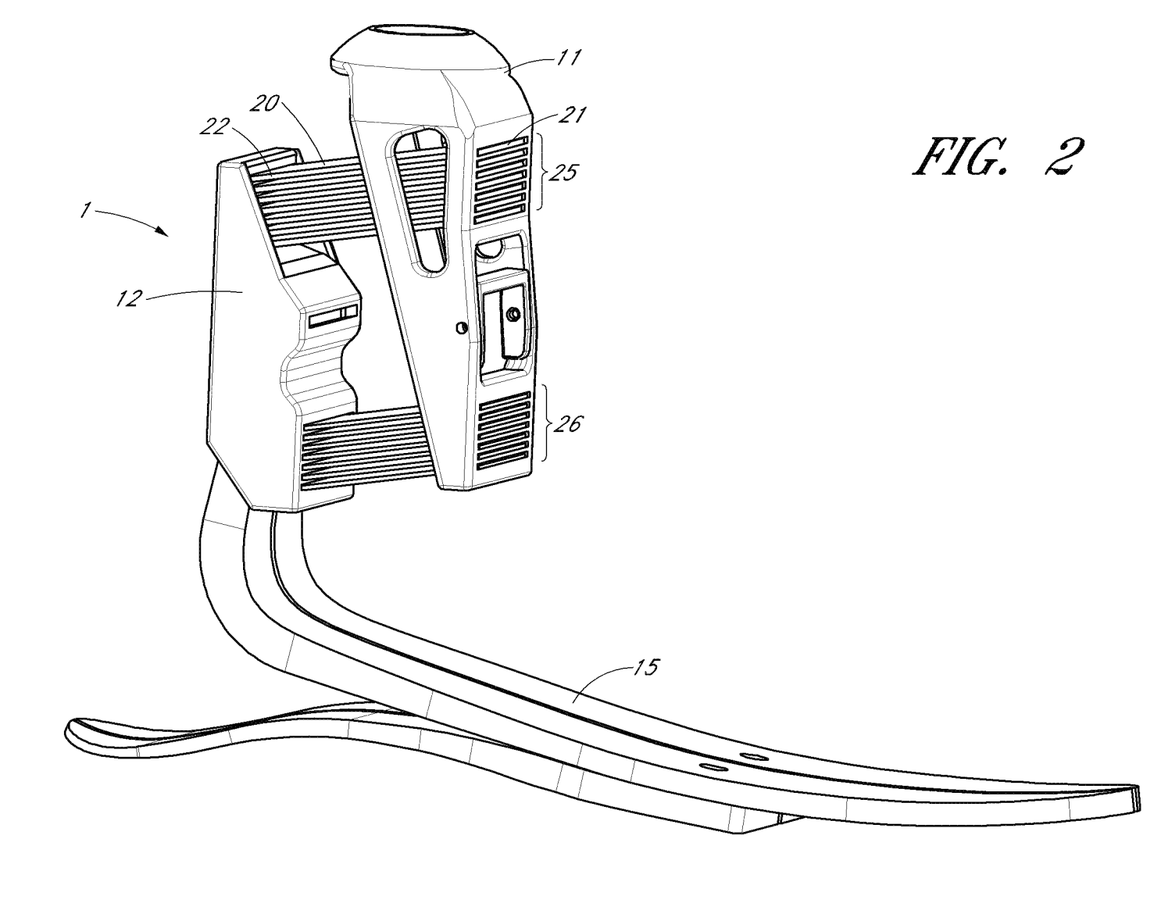
FIG. 2 is a schematic perspective side view of one embodiment of a frictionless vertical suspension member coupled to the prosthetic foot of FIG. 1.

The second member 12 can be coupled to the foot member 15. In some embodiments, the second member 12 is rigidly or fixedly coupled to the foot member 15 (e.g., via one or more fasteners (e.g., threaded fasteners), an adhesive (e.g., glue, epoxy), and/or a press-fit connection between the second member 12 and the foot member 15). With reference to FIG. 2, the second member 12 can have a recess (not shown) in to which the proximal section 13 of the prosthetic foot 100 can be inserted.

The first member 11 is movably coupled to the second member 12 through leaf springs 20. Each leaf spring 20 includes a first end 21 and a second end 22 and is generally plate-like (e.g., planar). As shown in FIG. 2, in one embodiment, the leaf springs 20 are generally rectangular and can readily flex in the longitudinal direction of the springs 20, but not in the transverse direction (e.g., along the width) of the springs 20. The first end 21 is the end of the leaf spring 20 nearest to the first member 11. The second end 22 is the end of the leaf spring 20 nearest to the second member 12. In one embodiment, the first end 21 can be rotationally fixed relative to the first member 11 and the second end 22 can be rotationally fixed relative to the second member 12. The leaf spring 20 is flexible such that applying a downward vertical force on the first member 11 and pressing the first member 11 towards the foot member 15 will cause the first member 11 to move relative to the second member 12. This relative movement between the first member 11 and the second member 12 enables vertical suspension between the person's leg and the foot member 15. As discussed in greater detail herein, the stiffness and suspension characteristics of the vertical suspension member 1 can be customized for individual users by varying, for example, the stiffness, length, and/or number of leaf springs 20 in the vertical suspension member 1.

Figure 6A:
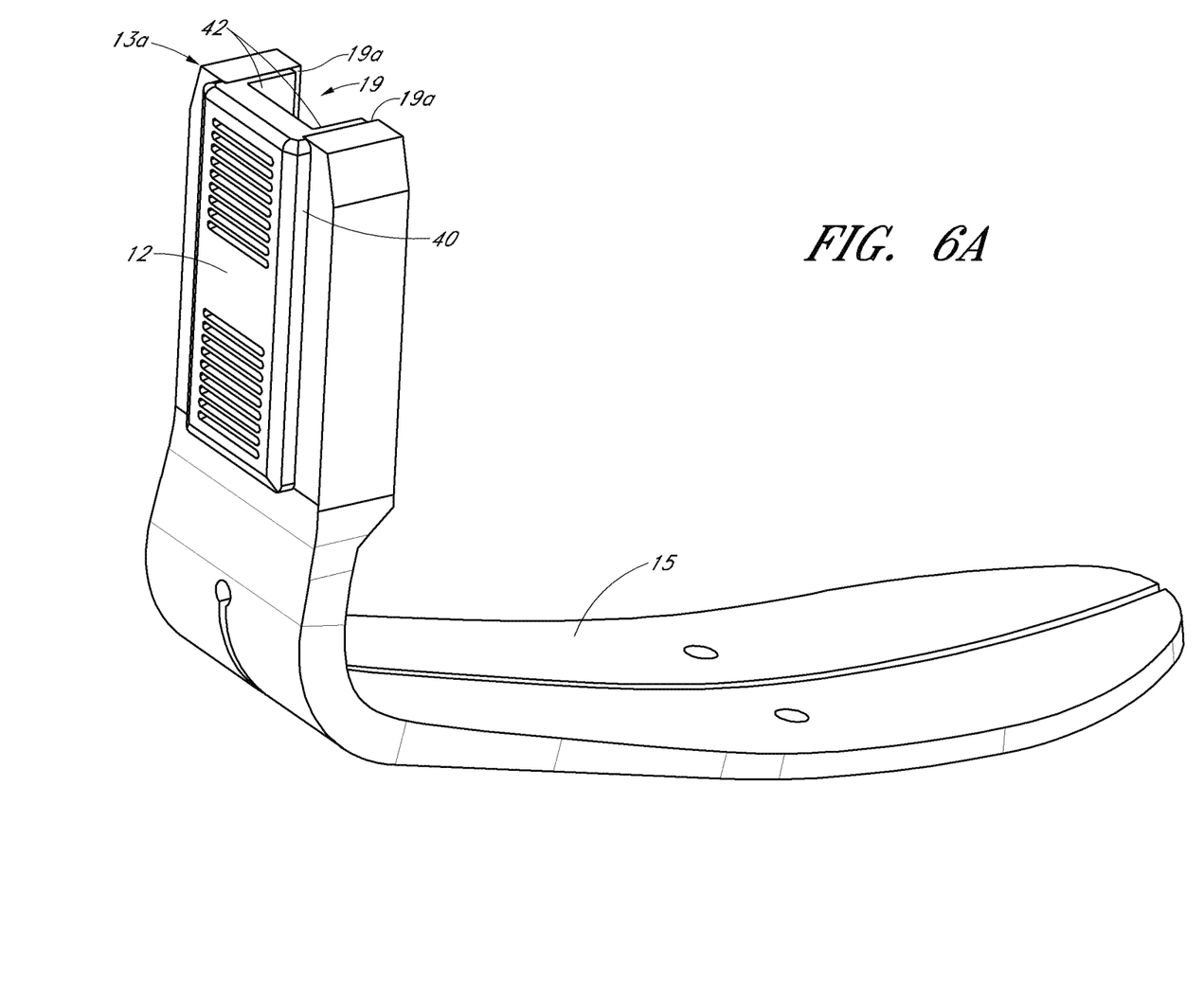
FIG. 6A is a schematic partial perspective rear view of one embodiment of a frictionless vertical suspension member portion coupled to a prosthetic foot.
Figure 6B:
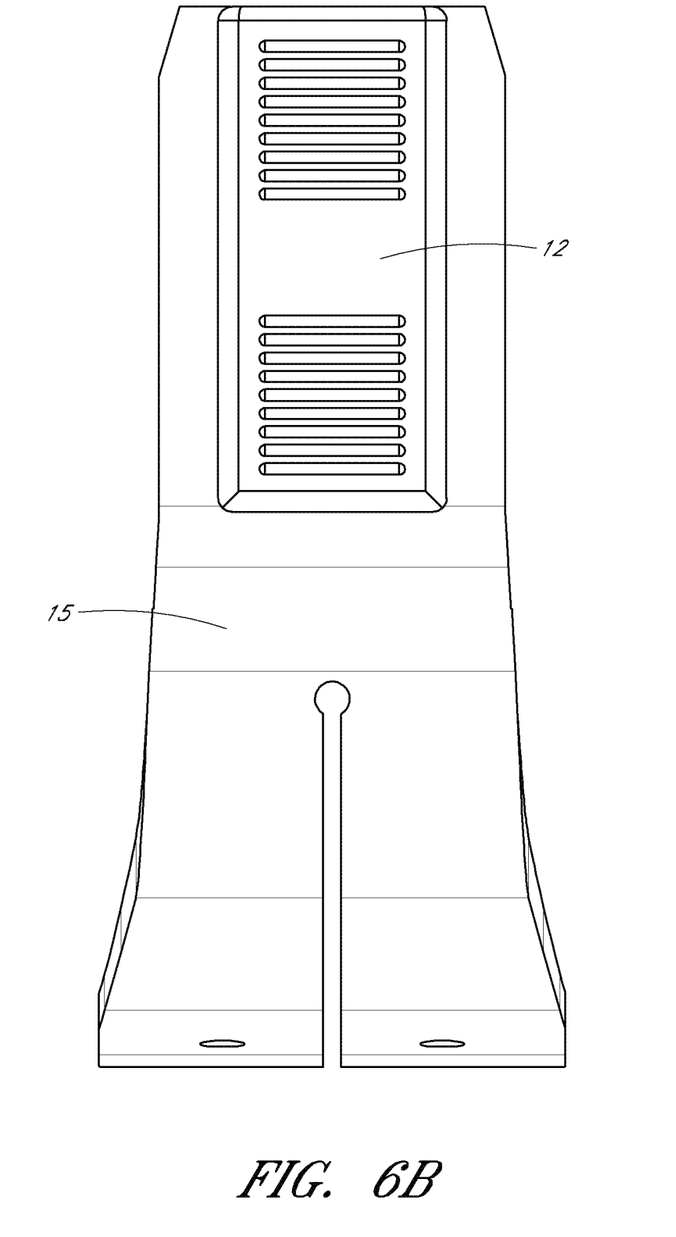
FIG. 6B is a schematic partial rear view of the frictionless vertical suspension member portion coupled to the prosthetic foot of FIG. 6A.
Figure 6C:
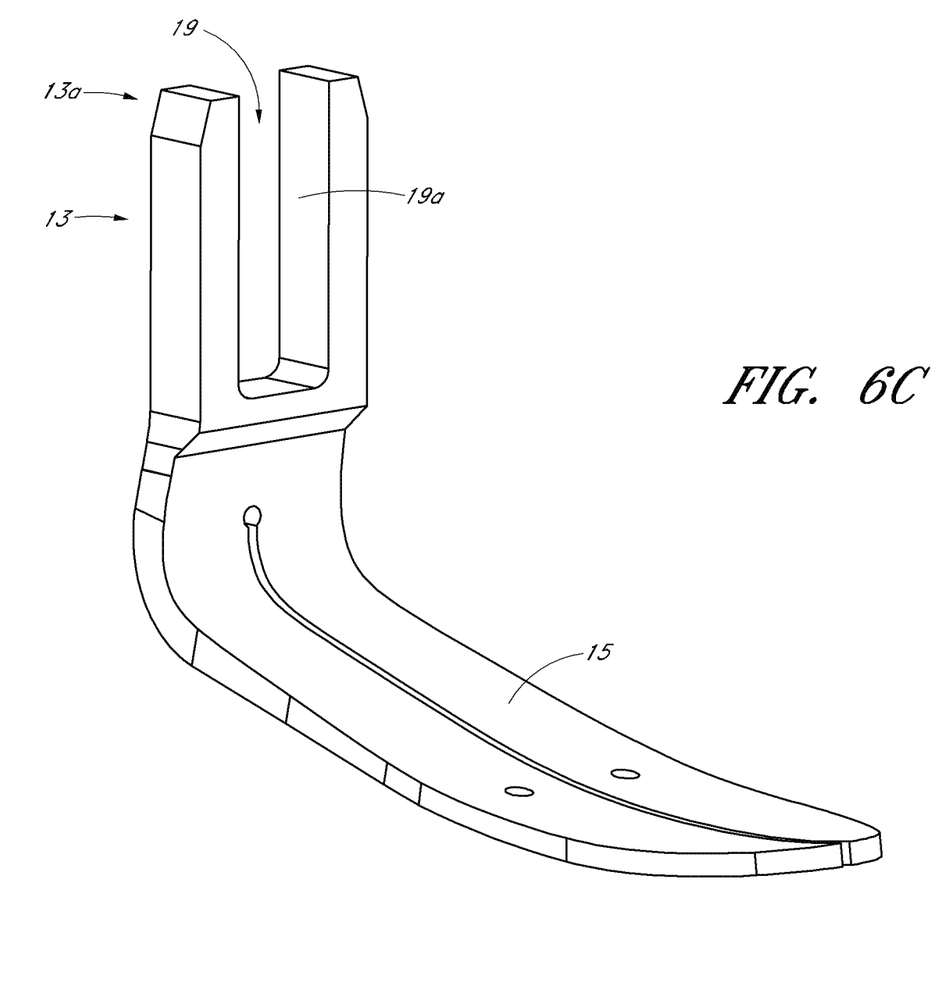
FIG. 6C is a schematic perspective front view of the prosthetic foot of FIG. 6A.

In one embodiment, the second member 12 is located between the ankle region and the thigh region. In another embodiment, the second member 12 is flexibly and/or movably coupled to the foot member 15. In yet another embodiment, for example the embodiment illustrated in FIGS. 6A and 6B, the second member 12 is integrated into the foot member 15. As shown in FIG. 6C, the foot member 15 includes a longitudinal recess 19 in the proximal section 13. In some embodiment, the recess 19 extends to the proximal end 13a of the foot member 15. The recess 19 defines two side walls 19a and is designed to receive (e.g., slidably receive) the second member 12, for example from a rear of the proximal section 13 (e.g., in a posterior-anterior direction) or from the proximal end 13a (e.g., in a vertical direction). The second member 12 is sized and shaped to slide or otherwise fit into the recess 19. The second member 12 can include a flange 40 sized and shaped to abut the rear surface of the foot member 15 and side walls 42 sized and shaped to extend into the recess 19 and abut the side walls 19a of the recess 19. In some embodiments, the second member 12 is secured to the foot member 15 via a press fit, an adhesive (e.g., glue, epoxy), or via any other suitable mechanisms. In another embodiment, a single part may include both the second member 12 and the proximal section 13 of the foot member 15, so that the second member 12 and the proximal section 13 of the foot member 15 are monolithic.

In at least some embodiments, e.g., those shown in FIGS. 2-5, the vertical suspension member 1 is an adapter that connects to a prosthetic foot or leg. The adapter can include the first member 11 and the leaf springs 20. The adapter may connect to a coupling device such as the second member 12 or the adapter may connect directly to a prosthetic foot and/or leg (e.g., couple directly to the proximal section 13 of the prosthetic foot 100).

In various embodiments, one or more leaf springs 20 couple the first member 11 to the second member 12. In some embodiments, the leaf springs 20 extend generally horizontally relative to a plane parallel to a ground surface between the first member 11 and second member 12 when the foot is at rest. In some embodiments, for example as shown in FIGS. 2-5, the leaf springs 20 extend from the second member 12 to the first member 11 at an angle with respect to a plane parallel to the ground surface. In some embodiments, the leaf springs 20 can be oriented at an angle of between about +/−20 degrees of being parallel to the ground. In some embodiments, the leaf springs 20 can be oriented at an angle of between about +/−30 degrees of being parallel to the ground. In some embodiments, the leaf springs 20 can be oriented at an angle of between about +/−45 degrees of being parallel to the ground. These are only sample angles and others are possible.

Figure 7A:
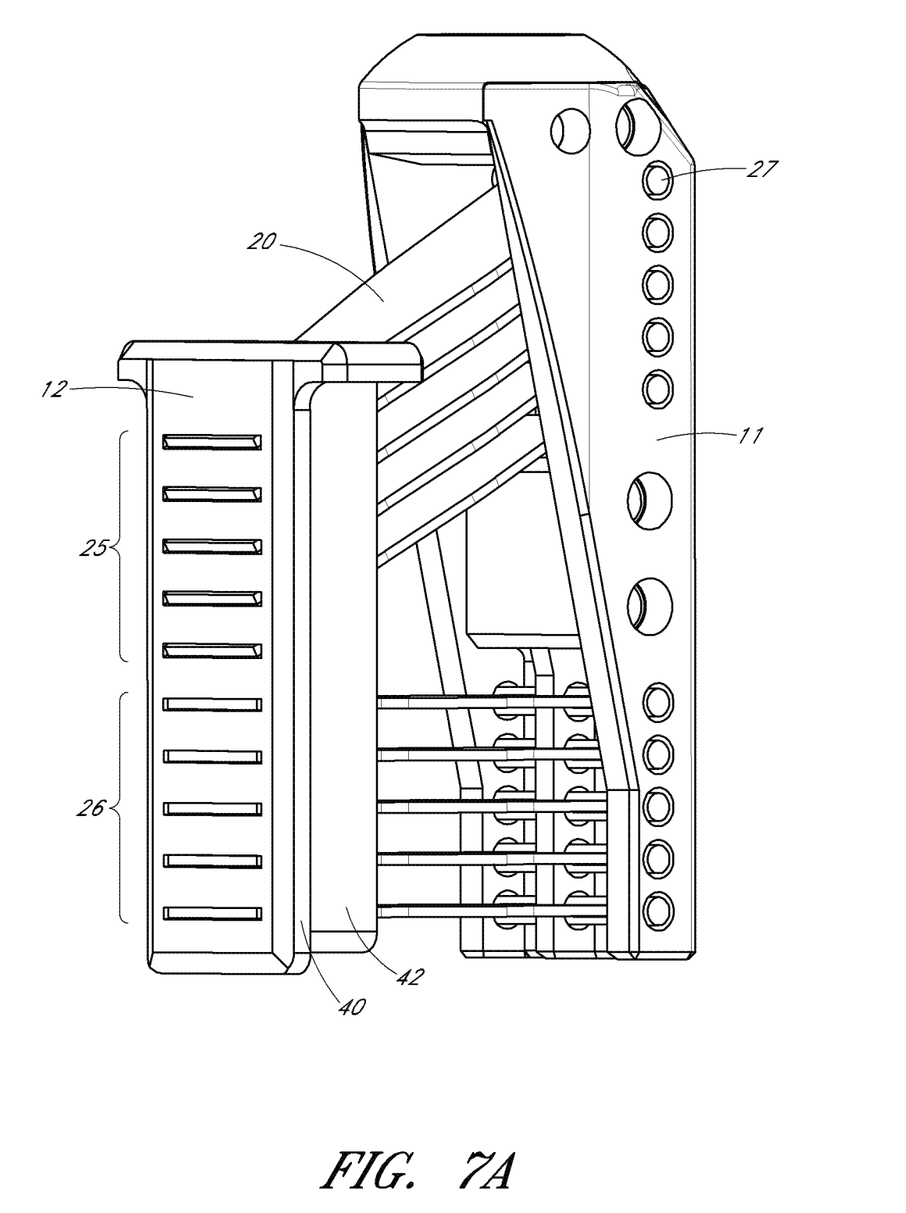
FIG. 7A is a schematic perspective rear view of one embodiment of a frictionless vertical suspension member for use with the prosthetic foot member of FIG. 6A.
Figure 7B:
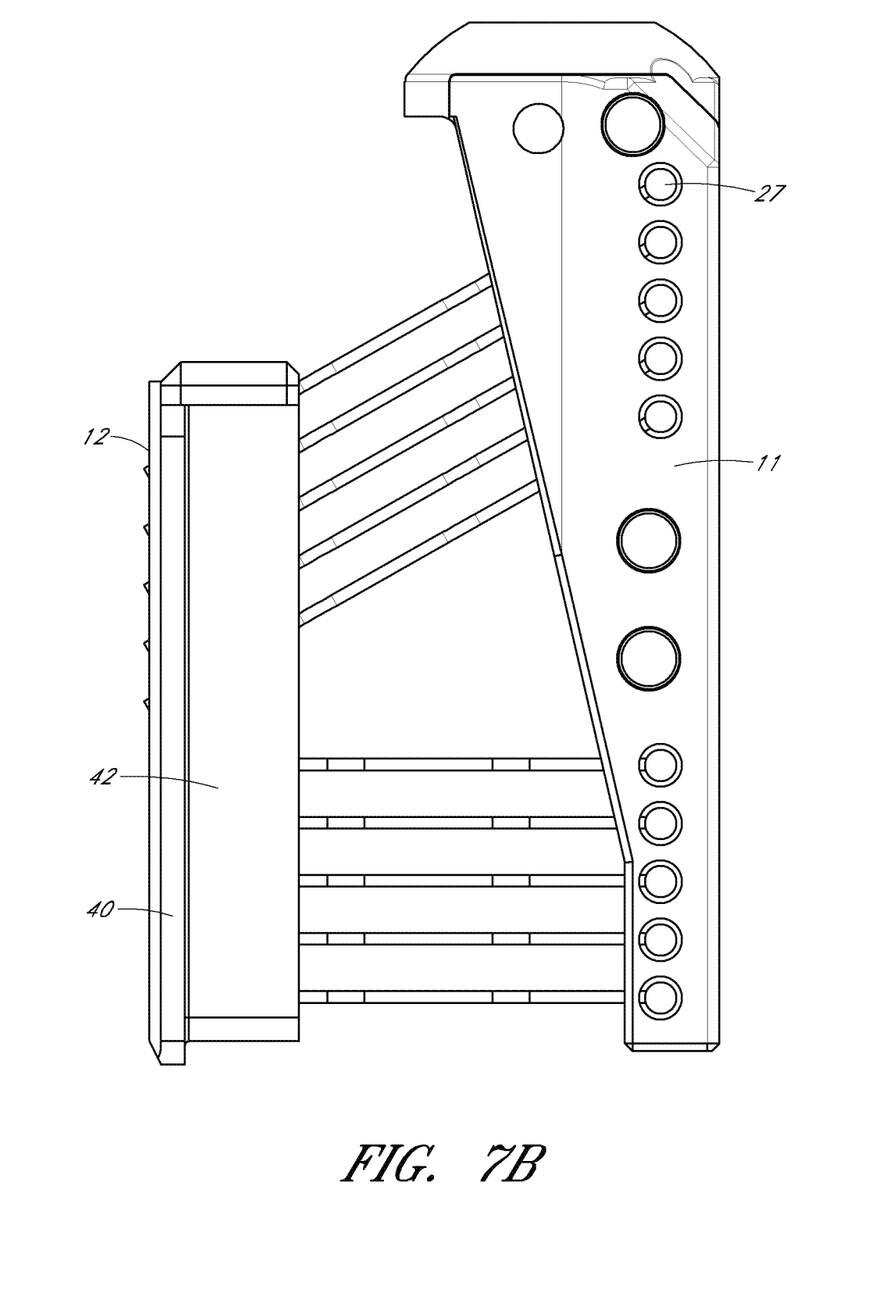
FIG. 7B is a schematic perspective side view of the frictionless vertical suspension member of FIG. 7A.

The leaf springs 20 can be rotationally fixed or pivotally attached to one or both of the first 11 and second 12 members. Rotationally fixed leaf spring portions cannot pivot relative to the member to which they are attached. Pivotally attached leaf spring portions can pivot relative to the member to which they are attached. In one embodiment, a pivotally attached leaf spring end can rotate approximately 10 degrees relative to the member to which it is attached. In one embodiment, at least a portion of at least one leaf spring 20 is rotationally fixed to the first member 11 and/or to the second member 12. In another embodiment, at least a portion of each leaf spring 20 is rotationally fixed to the first member 11 while at least a portion of each leaf spring 20 is attached to the second member 12 via a pivot such that at least a portion of each leaf spring 20 is able to rotate relative to the second member 12. In yet another embodiment, at least a portion of each leaf spring 20 is rotationally fixed to the second member 12 while at least a portion of each leaf spring 20 is attached to the first member 11 via a pivot such that at least a portion of each leaf spring 20 is able to rotate relative to the first member 11. For example, in the embodiment illustrated in FIGS. 7A and 7B, the leaf springs 20 are rotationally fixed to the second member 12 and coupled to the first member 11 via rolling pins 27. Such an arrangement can advantageously allow for rotation of the first member 11 if an upper stack 25 of leaf springs is oriented non-parallel to a lower stack 26 of leaf springs, as discussed in greater detail herein.

Leaf springs 20 may be secured to the first member 11 and/or to the second member 12 via welding, an interference fit, a snap fit, interlocking geometry, adhesives, and/or fasteners (e.g., screws). For example, a screw may pass through a hole in the end of the leaf spring 20 and through the first member 11 or through the second member 12 to secure the leaf spring 20 thereto. Leaf springs 20 may be attached to the first member 11 and/or to the second member 12 via a shackle (not shown), which is a swing arm. In various embodiments, the shackle can be about 0.75 mm to about 30 mm long between attachment points.

The leaf springs 20 can be flexible to allow the first member 11 to move relative to the second member 12. The leaf springs 20 can also have sufficient elasticity or resiliency to enable them to approximately return to their original position after the load that deforms the leaf springs 20 is removed (e.g., during a swing phase in the gait cycle of the prosthetic foot). The input force or load is the force between the first member 11 and the second member 12 due to the person wearing the prosthetic foot 100 striking or touching the ground. In one embodiment, the first end 21 can move at least 0.75 mm relative to the second end 22, compared to a zero input force state, when a force of about 450 N pushes the first member 11 towards the foot member 15 while the foot member 15 is stationary. In another embodiment, the first end 21 returns to within about 0.75 mm of its starting position when an input force of 450 N is removed. In some embodiments, the first end 21 can move between about 5 mm and about 20 mm relative to the second end 22 under applied loads of between about 500 N to about 3,000 N.

The leaf springs 20 can flex, bend, pivot, and/or arc due to the input force or load rather than compress in length such as when a soft pillar is compressed along its axis. In one embodiment, an orientation of the leaf springs 20 can vary over a range of +/−20 degrees relative to a plane parallel to the ground surface as the first member 11 is loaded and unloaded during use. For example, in the embodiment shown in FIG. 2, when the foot member 15 rests on the ground and the first member 11 is unloaded, the leaf springs 20 can be oriented upward toward the front of the foot, or at a positive angle with respect to a plane parallel to the ground, when viewed from the right side. As the first member 11 is loaded, the first member 11, and with it the first ends 21 of the leaf springs, can move generally vertically downward, causing the leaf springs to flex, bend, pivot, and/or arc so that the leaf springs become oriented downward toward the front of the foot, or at a negative angle with respect to a plane parallel to the ground when viewed from the right side. In another embodiment, the leaf springs 20 can vary over a range of +/−30 degrees relative to a plane parallel to the ground surface as the first member 11 is loaded and unloaded. In yet another embodiment, the leaf springs 20 can vary over a range of +/−45 degrees relative to a plane parallel to the ground surface as the first member 11 is loaded and unloaded. These are example angles, however, and others are possible.

Various embodiments include diverse leaf spring 20 materials. In one embodiment, the material of the leaf springs 20 can be hardened steel. In another embodiment, the material of the leaf springs 20 can be titanium. In yet another embodiment, the leaf springs 20 can be made from a composite material (e.g., carbon composite) with sufficient elasticity, resiliency and rigidity for the weight and physical activity of the person wearing the prosthesis. Example composite materials include unidirectional glass and/or carbon filaments or fibers in an epoxy matrix. In other embodiments, the leaf springs 20 can be made of fiber reinforced plastic or a mixture of graphite and epoxy. Different materials can produce leaf springs 20 having different stiffnesses.

The first member 11 and the second member 12 may be manufactured by milling stainless steel. In some embodiments, the first member 11 and second member 12 are made of aluminum. As noted above, the foot member 15 may comprise carbon fiber. In one embodiment, the foot member 15 is manufactured by combining carbon fibers with plastic resin.

The leaf springs 20 may have uniform cross-sectional geometries or they may have non-uniform cross-sectional geometries. In one embodiment, the leaf springs 20 have a length and width that makes them rectangular. In one embodiment, the leaf springs 20 can have a thickness that is less than 50% of the leaf springs' 20 length and width. In the embodiment shown in FIG. 2, each leaf spring 20 has a thickness that is less than 15% of the leaf spring's 20 length and width. The leaf springs 20 can also be flat springs or cantilever springs.

In another embodiment, the leaf springs 20 can be trapezoidal cantilever springs. The trapezoidal cantilever springs can have non-uniform cross-sectional geometries. In one embodiment, the leaf springs 20 can have non-uniform thicknesses along their lengths. For example, the leaf springs 20 may be thicker near the first member 11 than near the second member 12. In another embodiment, the leaf springs 20 can have non-uniform widths. For example, each leaf spring 20 may be 20 mm wide at the first end 21 and 30 mm wide at the second end 22. In some embodiments, the leaf springs 20 may be flat or curved.

In some embodiments, the first 11 and second 12 members can be coupled by two sets of leaf springs, an upper stack 25 and a lower stack 26. For example, the embodiments shown in FIGS. 2-5 include 14 leaf springs 20. The leaf springs 20 are divided into two groups of 7. An upper stack 25 comprises 7 leaf springs 20 and a lower stack 26 comprises 7 leaf springs 20. As shown, in some embodiments, when the foot member 15 rests on the ground and the first member 11 is unloaded, the first member 11, second member 12, upper stack 25 of leaf springs, and lower stack 26 of leaf springs can be arranged so as to generally form a parallelogram oriented upward toward the front of the foot when viewed from the right side. As the first member 11 is loaded, the first member 11, and with it the first ends 21 of the leaf springs, can move generally vertically downward, causing the leaf springs to flex, bend, pivot, and/or arc. Although the first member 11, second member 12, upper stack 25 of leaf springs, and lower stack 26 of leaf springs can generally retain a parallelogram shape when loaded, the downward movement of the first member 11 causes the parallelogram to shift to being oriented downward toward the front of the foot when viewed from the right side. In other embodiments, each stack comprises between 1 and 1,000 leaf springs 20. For example, the embodiment shown in FIGS. 7A and 7B includes an upper stack 25 having 5 leaf springs 20 and a lower stack 26 having 5 leaf springs 20. Varying the number of leaf springs 20 can allow for variations in overall stiffness of the suspension member 1. In one embodiment, each leaf spring 20 consists of multiple layers. In the illustrated embodiment, the leaf springs 20 are generally parallel to each other. In another embodiment, the leaf springs 20 can be within 10 degrees of being parallel to each other. As mentioned above, FIGS. 7A and 7B illustrate an embodiment in which the upper stack 25 of leaf springs 20 is non-parallel to the lower stack 26 of leaf springs. Such a non-parallel configuration can allow for different movements of the various components of the vertical suspension member 1 relative to one another. For example, when loaded, the first member 11 can pivot in an anterior-posterior plane off vertical as it moves down. A non-parallel arrangement can also result in leaf springs of different lengths, which can alter stiffness properties of the leaf springs and vertical suspension member 1.

FIGS. 2-5 illustrate embodiments wherein the leaf springs 20 in the upper stack 25 do not touch each other and the leaf springs 20 in the lower stack 26 do not touch each other. Leaf springs 20 that do not touch other leaf springs 20 in the region of the leaf springs 20 that bend are called independently flexing leaf springs. One advantage of this arrangement is that the leaf springs 20 do not create friction by rubbing together, thereby inhibiting energy loss in the vertical suspension member 1 during use of the prosthetic foot 100. The leaf springs 20 can flex to store the input energy as potential energy. The leaf springs 20 can then release said potential energy to the user when they return to their zero input force position (e.g., to propel the prosthetic foot into toe-off during ambulation).

In another embodiment, leaf springs 20 can rub against each other and the friction created by rubbing of the springs can dampen movement between the first member 11 and the second member 12. This damping can reduce vibrations and/or oscillations between the first member 11 and the second member 12.

In the illustrated embodiments, the leaf springs 20 are arranged so that the first 21 and second 22 ends of each leaf spring 20 are generally horizontal. However, in some embodiments, the first 21 and/or second 22 ends of one or more leaf springs 20 can be arranged generally not horizontally, e.g., tilted in the coronal plane. Such an arrangement can advantageously provide stiffer suspension and/or allow for inversion and/or eversion of the foot during use.

Figure 3:
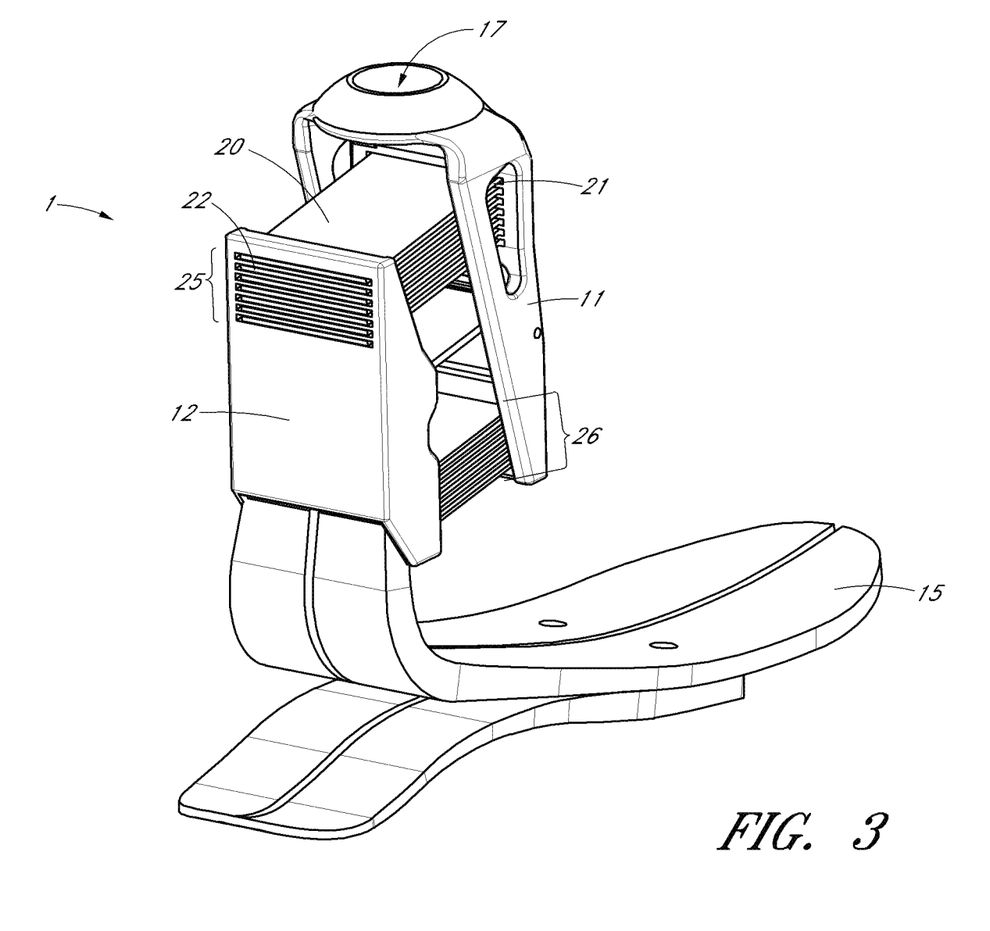
FIG. 3 is a schematic perspective rear view of another embodiment of a frictionless vertical suspension member coupled to the prosthetic foot of FIG. 1.
Figure 4:
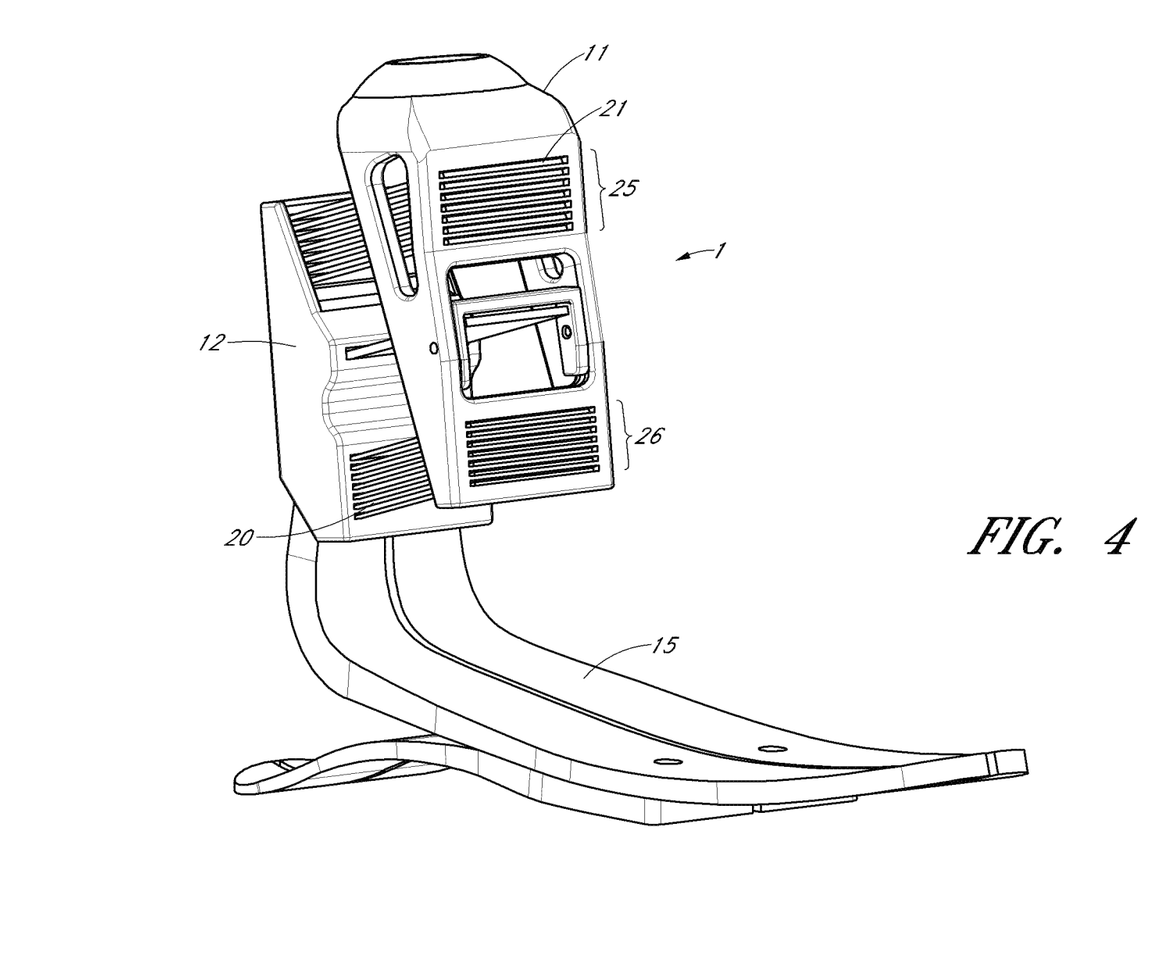
FIG. 4 is a schematic perspective front view of the frictionless vertical suspension member of FIG. 3 coupled to the prosthetic foot of FIG. 1.
Figure 5:
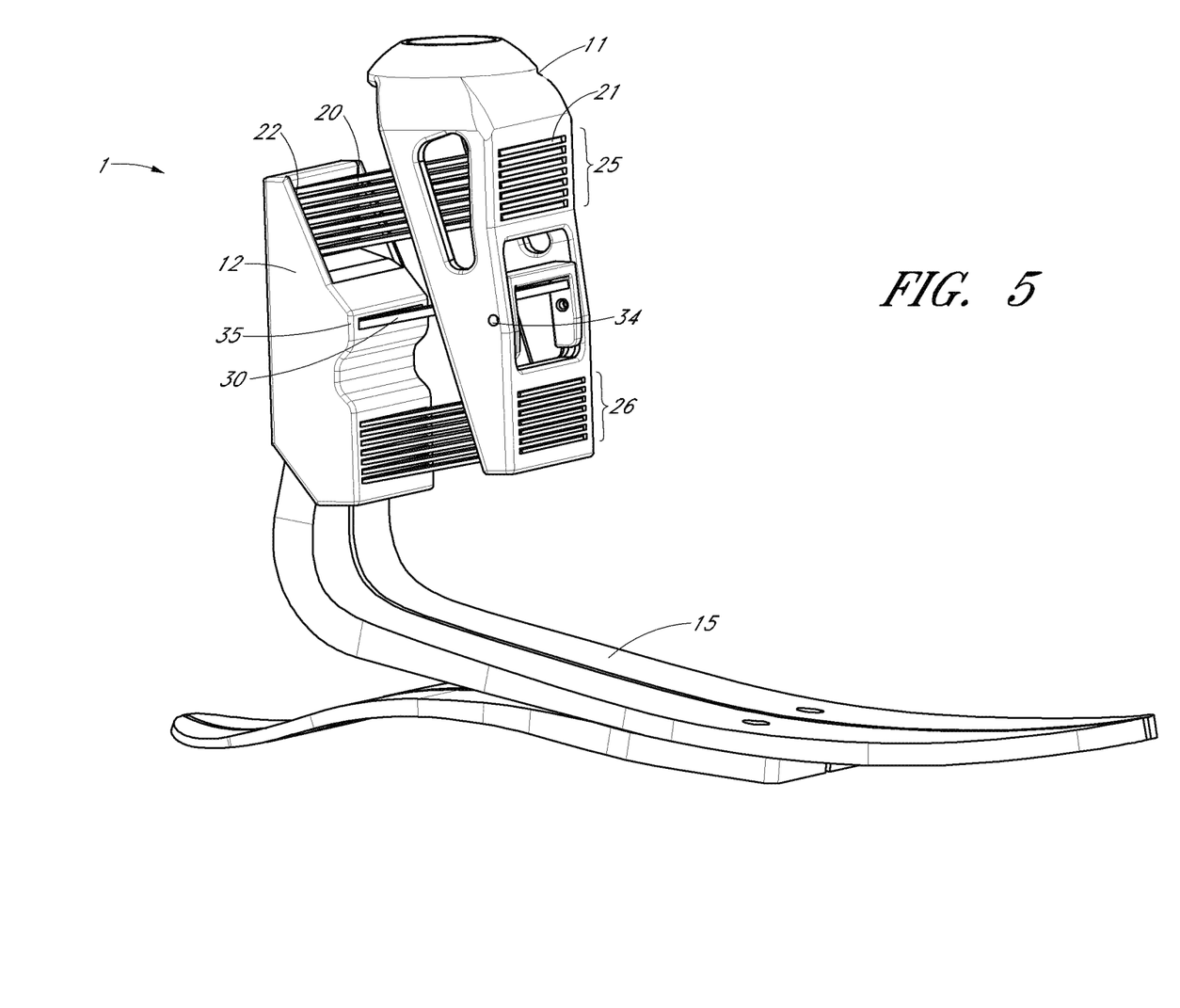
FIG. 5 is a schematic perspective side view of the frictionless vertical suspension member of FIG. 3 coupled to the prosthetic foot of FIG. 1.

FIGS. 3-5 show a variable stiffness embodiment of the vertical suspension member 1. This embodiment includes an adjustable leaf spring 30. The adjustable leaf spring 30 can be fixed on one end. The other end of the adjustable leaf spring 30 can be grabbed, secured, clasped, and/or captured.

A pivot 34 can fix (e.g., grab, secure) the adjustable leaf spring 30 to the first member 11. The adjustable leaf spring 30 can be fixed to the second member 12 by a clamp 35. When the clamp 35 is open, the adjustable leaf spring 30 is free to slide in and out of the clamp 35 (e.g., can be adjusted by a user). When the clamp 35 is closed, the adjustable leaf spring 30 is not free to slide in and out of the clamp 35.

Sliding more of the adjustable leaf spring 30 into the region between the pivot 34 and the clamp 35 increases the length of the adjustable leaf spring 30 between the pivot 34 and the clamp 35. Altering the length of the adjustable leaf spring 30 between the pivot 34 and the clamp 35 influences the stiffness of the vertical suspension member 1. For example, reducing the length of the adjustable leaf spring 30 between the pivot 34 and the clamp 35 increases the stiffness of the prosthesis.

When the clamp 35 is open, a person such as a physician, prosthetic technician, or prosthetic owner can adjust the adjustable leaf spring 30 by altering the length of the adjustable leaf spring 30 that is captured between the pivot 34 and the clamp 35. Once the adjustable leaf spring 30 is in the desired position, a person can close the clamp 35 to secure the adjustable leaf spring 30. The person can try various lengths to determine which length results in the desired stiffness.

Although many methods of use are possible, one method includes flexing leaf springs 20 which are part of a prosthesis by applying weight to a prosthetic foot. Another method includes attaching a human leg to a prosthetic foot, such as the prosthetic foot 100, applying weight to a prosthetic foot by walking, and flexing leaf springs 20 that couple the first member 11 to the second member 12.

Although the invention is described above with respect to prosthetic feet, the invention can be used with other parts of the body, including, for example, in a full-leg prosthesis wherein the suspension system is located in the thigh or knee regions (e.g., in a location above the knee). Additionally, one or ordinary skill in the art will recognize that the use of a vertical suspension member having the features described above (e.g., leaf springs) is not limited to prosthetics and can be incorporate in other applications to provide relatively lightweight vertical suspension with reduced friction.

Of course, the foregoing description is that of certain features, aspects and advantages of the present invention, to which various changes and modifications can be made without departing from the spirit and scope of the present invention. Moreover, the vertical suspension member need not feature all of the objects, advantages, features and aspects discussed above. Thus, for example, those skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of the specific features and aspects between and among the different embodiments may be made and still fall within the scope of the invention, and that the invention has applicability in vertical suspension in general, and is not limited to prosthetics. Accordingly, it should be understood that various features and aspects of the disclosed embodiments can be combined with or substituted for one another in order to form varying modes of the discussed vertical suspension member.

What is claimed is:
1. A suspension system, comprising:
a first member generally extending along an axis when the suspension system is in use and unloaded;
a second member having a first end and an opposite second end, the second member spaced apart from and disposed across from the first member, the first member being movable relative to the second member, wherein when the suspension system is in use and unloaded, the second member is generally parallel to the first member;
a first plurality of spaced-apart leaf springs extending generally transversely between and attached to the first member and the second member, a topmost leaf spring of the first plurality of leaf springs located at or near a first end of the second member on one end of the topmost leaf spring and at a location between and away from the first and second ends of the first member on an opposite end of the topmost leaf spring; and
a second plurality of spaced-apart leaf springs extending generally transversely between and attached to the first member and the second member, a bottommost leaf spring of the second plurality of leaf springs located at or near a second end of the second member,
wherein the first plurality of spaced-apart leaf springs are spaced from and generally parallel to the second plurality of spaced-apart leaf springs when the suspension system is in use and unloaded, the first and second pluralities of spaced-apart leaf springs separated by a first distance, and distances between adjacent leaf springs of the first plurality of spaced-apart leaf springs and distances between adjacent leaf springs of the second plurality of spaced-apart leaf springs being smaller than the first distance, and
wherein the first and second pluralities of leaf springs are separated by a distance that is greater than half of a length of the second member.

2. The suspension system of claim 1, wherein the topmost leaf spring of the first plurality of leaf springs and the bottommost leaf spring of the second plurality of leaf springs are separated by a distance that is substantially the same as a length of the second member.

3. The suspension system of claim 1, wherein the second member comprises a plurality of slots, each slot configured to receive one of the leaf springs of the first or second plurality of leaf springs.

4. The suspension system of claim 1, wherein the first plurality of leaf springs are generally parallel to one another when the suspension system is in an unloaded state.

5. The suspension system of claim 4, wherein the second plurality of leaf springs are generally parallel to one another when the suspension system is in an unloaded state.

6. The suspension system of claim 1, wherein each of the leaf springs comprises a planar leaf spring.

7. The suspension system of claim 1, wherein the first member comprises a plurality of slots, each slot configured to receive one of the leaf springs of the first or second plurality of leaf springs.

8. The suspension system of claim 7, wherein the first and second pluralities of leaf springs are coupled to the first and second members solely by the plurality of slots on the first member and a plurality of slots on the second member.

9. The suspension system of claim 1, wherein, when the suspension system is in use and unloaded, the second member has a generally vertically extending longitudinal axis generally parallel to a generally vertically extending longitudinal axis of the first member and the plurality of leaf springs extend generally transversely to the generally vertically extending longitudinal axes of the first and second members, the generally vertically extending longitudinal axis of the first member being horizontally spaced from and disposed across from the generally vertically extending longitudinal axis of the second member.

10. A suspension system, comprising:
a first member generally extending along an axis when the suspension system is in use and unloaded, the first member having a first end and a second end;
a second member having a first end and an opposite second end, the second member spaced apart from and disposed across from the first member, the second member having a first end and a second end, the first member being movable relative to the second member, wherein when the suspension system is in use and unloaded, the second member is generally parallel to the first member, wherein the second member comprises a plurality of slots, each slot configured to receive one of the leaf springs of the first or second plurality of leaf springs;
a first plurality of leaf springs extending between the first and second members near the first ends of the first and second members; and
a second plurality of leaf springs between the first and second members, one end of the second plurality of leaf springs coupled to the second member near a second end of the second member, an opposite end of the second plurality of leaf springs coupled to the first member at a location between and away from the first and second ends of the first member, wherein the first plurality of leaf springs are generally parallel to the second plurality of leaf springs when the suspension system is in use and unloaded.

11. The suspension system of claim 10, wherein a topmost leaf spring of the first plurality of leaf springs and a bottommost leaf spring of the second plurality of leaf springs are separated by a distance that is substantially the same as a length of the second member.

12. The suspension system of claim 10, wherein the first and second pluralities of leaf springs are separated by a distance that is greater than half of a length of the second member.

13. The suspension system of claim 10, wherein the first plurality of leaf springs are generally parallel to one another when the suspension system is in an unloaded state.

14. The suspension system of claim 13, wherein the second plurality of leaf springs are generally parallel to one another when the suspension system is in an unloaded state.

15. The suspension system of claim 10, wherein each of the leaf springs comprises a planar leaf spring.

16. The suspension system of claim 10, wherein the first member comprises a plurality of slots, each slot configured to receive one of the leaf springs of the first or second plurality of leaf springs.

17. The suspension system of claim 16, wherein the first and second pluralities of leaf springs are coupled to the first and second members solely by the plurality of slots on the first member and a plurality of slots on the second member.

18. The suspension system of claim 10, wherein, when the suspension system is in use and unloaded, the second member has a generally vertically extending longitudinal axis generally parallel to a generally vertically extending longitudinal axis of the first member and the plurality of leaf springs extend generally transversely to the generally vertically extending longitudinal axes of the first and second members, the generally vertically extending longitudinal axis of the first member being horizontally spaced from and disposed across from the generally vertically extending longitudinal axis of the second member.

* * * * *